US00PP26074P2

(12) United States Plant Patent
Babikow

(10) Patent No.: US PP26,074 P2
(45) Date of Patent: Nov. 10, 2015

(54) ***PANICUM VIRGATUM* PLANT NAMED 'HOT ROD'**

(50) Latin Name: *Panicum virgatum*
Varietal Denomination: Hot Rod

(71) Applicant: Paul David Babikow, Pensacola, FL (US)

(72) Inventor: Paul David Babikow, Pensacola, FL (US)

(73) Assignee: Emerald Coast Growers, LLC, Pensacola, FL (US)

( * ) Notice: Subject to any disclaimer, the term of this patent is extended or adjusted under 35 U.S.C. 154(b) by 0 days.

(21) Appl. No.: 13/986,403

(22) Filed: Apr. 29, 2013

(51) Int. Cl.
*A01H 5/00* (2006.01)

(52) U.S. Cl.
USPC ..... Plt./384

(58) Field of Classification Search
USPC ..... Plt./384
See application file for complete search history.

*Primary Examiner* — Keith O. Robinson
(74) *Attorney, Agent, or Firm* — J. Nevin Shaffer, Jr.

(57) ABSTRACT

A new and distinct, vigorous cultivar of *Panicum virgatum* named 'Hot Rod' characterized by an upright growth habit and the development of red purple color in late spring early summer. The early development of color adds early season value as an ornamental.

4 Drawing Sheets

BACKGROUND OF THE INVENTION

The present invention relates to a new and distinct cultivar of Switchgrass botanically known as *Panicum virgatum* and hereinafter referred to by the name 'Hot Rod'. 'Hot Rod' is a new and distinct cultivar found as a chance seedling in summer 2008 at a plant nursery in Lancaster, Pa. Asexual propagation in the form of division has proven stable and true to type in successive generations. Although phenotypic variations may occur depending on environmental factors such as light intensity, fertility and water there is no change in the plant's genotype.

SUMMARY OF THE INVENTION

*Panicum virgatum* (Switchgrass) is a native North American prairie grass occurring throughout the central and eastern United States. 'Hot Rod' was selected for its upright growth habit, red foliage, and red seed heads. 'Hot Rod' is easily propagated by division and has a vigorous, compact, clumping growth habit. 'Hot Rod' has been grown to mature size over multiple seasons in Lancaster, Pa.; Pensacola, Fla.; and West Lafayette, Ind.; showing it to be similar to other switchgrasses in its ability to tolerate a wide range of soils and temperatures.

'Hot Rod' differs from the species in that it has a blue green basal color and develops red foliage; it differs from other known cultivars that develop red foliage in that 'Hot Rod' develops its red purple color in late spring/early summer. The early development of color adds early season value as an ornamental.

Table 1 compares the closest known *Panicum virgatum* cultivars: 'RR1' U.S. Plant Pat. No. 17,944, 'Prairie Fire' U.S. Plant Pat. No. 19,367, and 'Shenandoah' (unpatented). All three similar cultivars develop red foliage later in the season when compared to 'Hot Rod'. 'Hot Rod' is smaller in stature than 'Shenandoah' and 'Prairie Fire', but taller than 'RR1'; it also has more erect leaves when compared to 'RR1' and 'Shenandoah'.

TABLE 1

| Cultivar | Foliage Height (cm) | Growth Habit | Initial Foliage Color | Season of Red Color Development |
|---|---|---|---|---|
| 'Hot Rod' | 90 | Upright | Blue-green | Early (May-June) |
| 'Shenandoah' | 140 | Arching | Blue-green | Late (July-August) |
| 'RR1' | 55 | Upright | Blue-green | Mid (July) |
| 'Heavy Metal' | 130 | Upright | Blue-green | None |
| 'Prairie Fire' | 100 | Upright | Blue-green | Mid (July) |
| 'Rotstrahlbusch' | 110 | Upright | Green | Late (August) |
| 'Haense Herms' | 100 | Upright | Green | Late (August) |

DESCRIPTION OF THE PHOTOGRAPHS

The accompanying colored photographs illustrate the overall appearance of the new plant showing the colors as true as it is reasonably possible to obtain in colored reproductions of this type. Colors in the photographs may differ slightly from the color values cited in the detailed botanical description which accurately describe the colors of the new plant.

Figure 1:
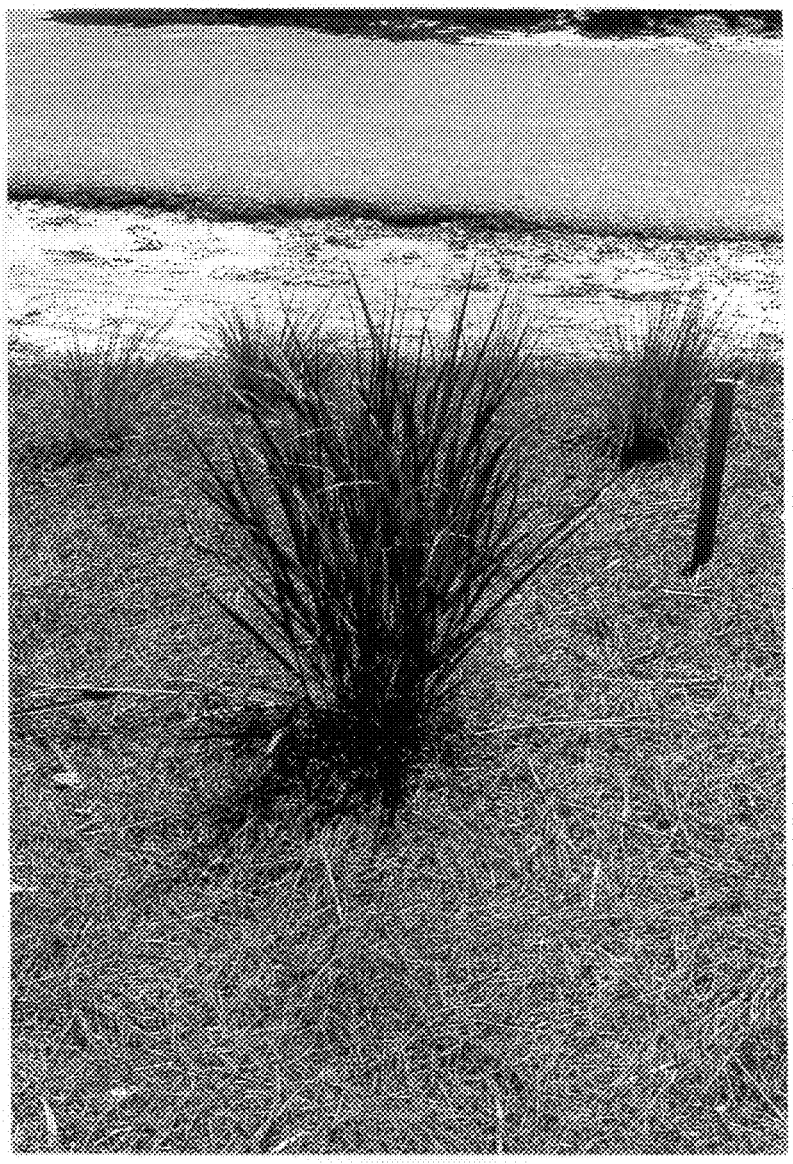

The photograph in FIG. 1 on the first sheet shows the early development of red color in the leaves of the 'Hot Rod' plant in early spring.

Figure 2:
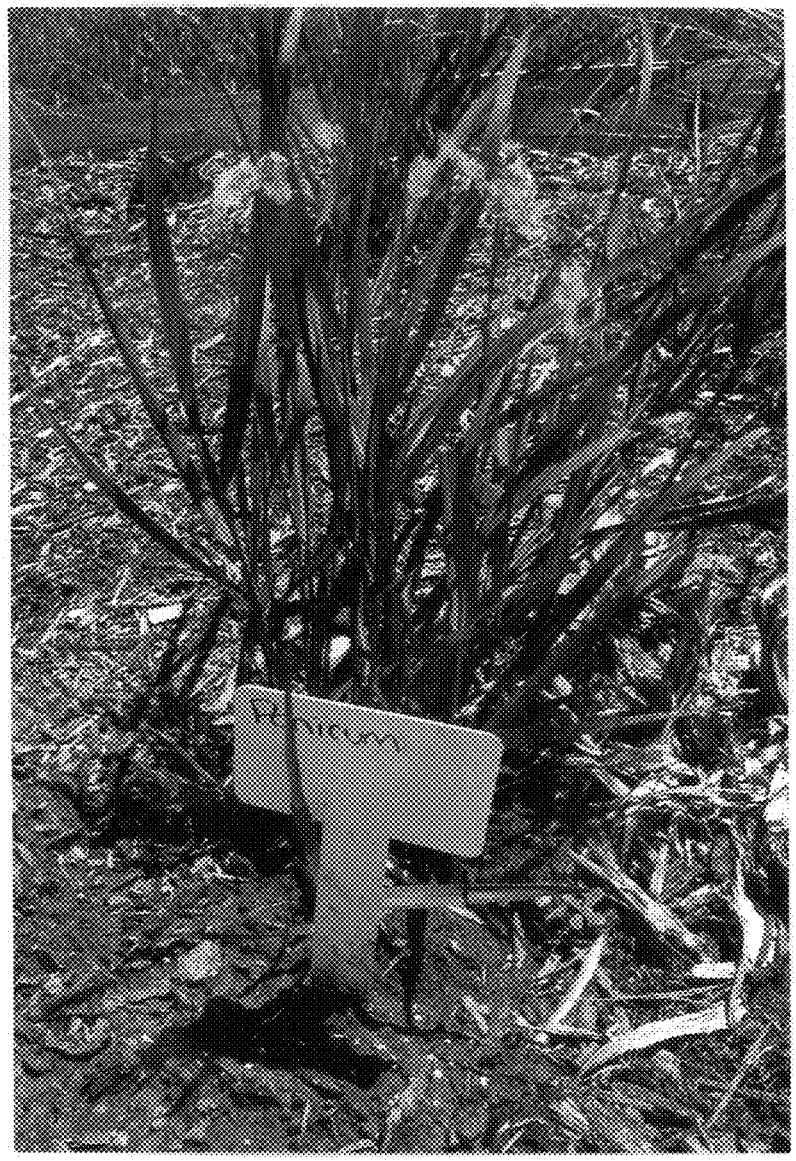

The photograph in FIG. 2 on the second sheet shows the further development of red color and growth form in midsummer.

Figure 3:
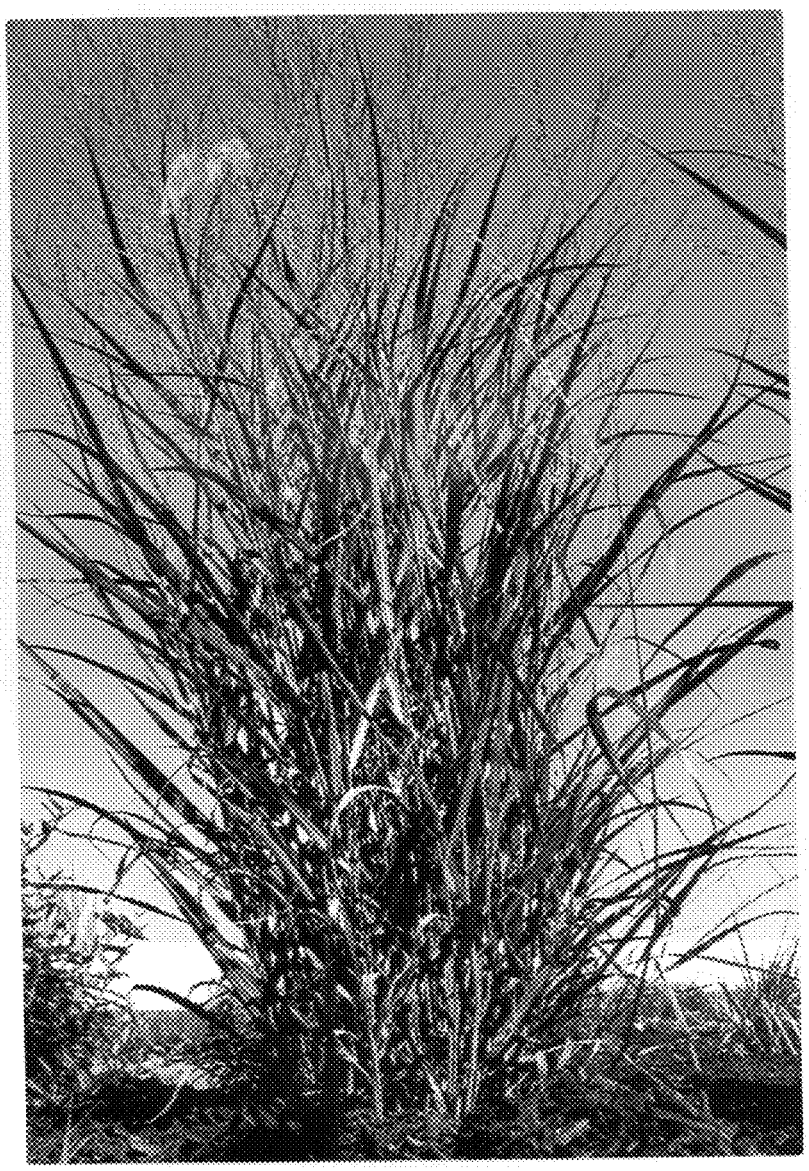

The photograph in FIG. 3 on the third sheet shows the color and growth form in late summer early fall.

Figure 4:
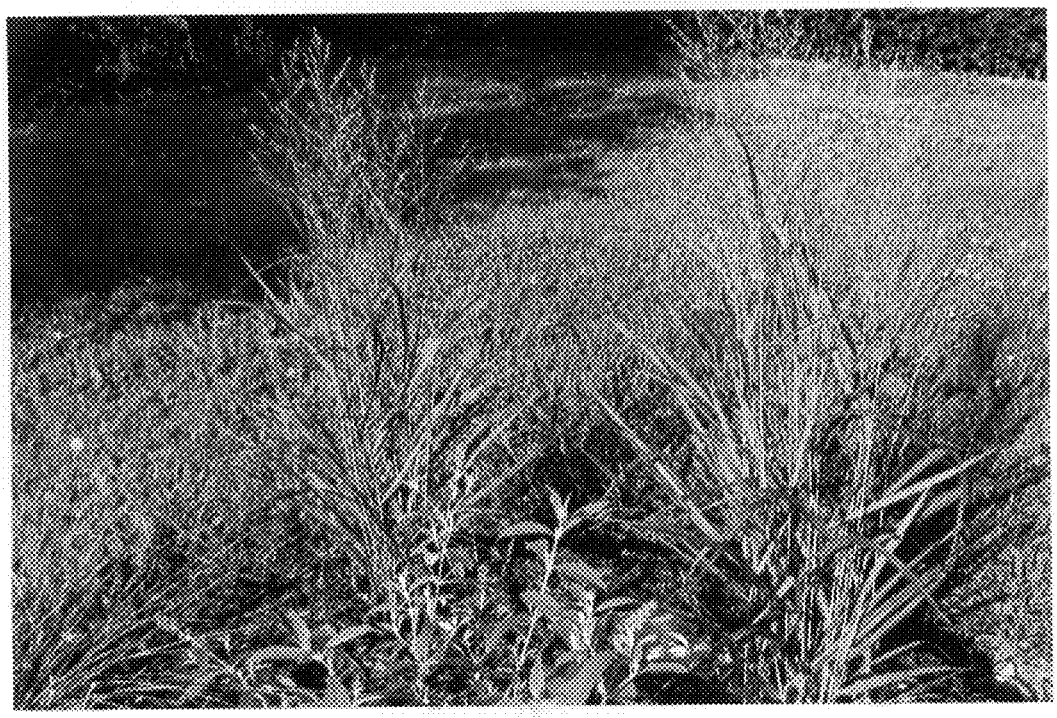

The photograph in FIG. 4 shows the inflorescence of the 'Hot Rod' plant in late summer.

DETAILED BOTANICAL DESCRIPTION

The aforementioned photographs and following observations and measurements of the new variety of *Panicum* describe two year old plants grown in full sun outdoor conditions in a trial garden located in Pensacola, Fla. The following color references are based on the 2007 edition of The Royal Horticultural Society Colour Chart except when common dictionary terms are used.

Parantage: Naturally-occurring chance seedling of *Panicum virgatum*.

Propagation:

*Method.*—By division of the culms. Culm is erect, enclosed by leaf sheath, 89 to 91 cm long with panicle and 0.5-3.5 mm in diameter; internodes 8 to 12 cm in length; RHS Green Group N138D.

*Root description.*—White, RHS NN155A, and fleshy when emerging and tan, RHS 164D, when mature. 2-3 weeks to initiate roots.

*Rooting habit.*—Fibrous.

Plant description:

*Plant shape and habit.*—Herbaceous perennial grass with an upright vase shape and compact habit.

*Plant size.*—Foliage height at flowering is 91 cm from soil base to top of the leaves and 23 cm wide at soil and 76 cm at the widest point.

Foliage description:

*Arrangement.*—Alternate, sheathed, erect.

*Shape.*—Linear.

*Margin.*—Entire.

*Aspect.*—Flat.

*Length.*—26-34 cm.

*Width.*—1-1.2 cm.

*Texture.*—Upper and lower surfaces smooth and glaucous.

*Color.*—Top surface early season: RHS N187A mature foliage; RHS N137A new emerging foliage. Underside early season: RHS N187B mature foliage; RHS N137B New emerging foliage. Top surface mid to late season: RHS 187A. Underside mid to late season: RHS 187B.

Flower description:

*Inflorescence.*—Fine textured, branched open panicles held mostly above the foliage.

*Natural flowering season.*—Flowering from early August with peak flower clusters in September. Panicle presence persists through winter.

*Panicle length.*—20-25.5 cm.

*Panicle width.*—10-12 cm.

*Panicle color.*—RHS Green Group N138C.

*Glumes.*—Lower outside 1-2.2 mm long and 1.5 mm wide RHS 187A, upper 2-3.8 mm long.

*Spikelet.*—5.5-6 mm long.

*Fragrance.*—None.

*Pedicel.*—0.5 to 1 mm in length and 0.16 mm wide; RHS Green Group 139D.

*Lemma.*—Lower 3.5 mm in length and 1.5 mm wide, RHS 187A; upper 3.0 mm in length and 1.2 mm wide, RHS 187A.

*Fruit.*—2 to 2.5 mm in length and 1.5 mm wide, RHS 199B.

*Pollen color.*—RHS 173A.

Pest and disease resistance: Similar to other *Panicum* species. Mildly resistant to *Panicum* Rust, *Puccinia emaculata*. No other pests or diseases were observed as is typical for this species.

*Temperature tolerance.*—USDA Zones 4-10.

*Drought tolerance/resistance.*—Drought resistant once mature and established.

What is claimed is:

1. A new and distinct cultivar of *Panicum virgatum* plant named 'Hot Rod' as illustrated and described.

* * * * *